US006548733B2

(12) United States Patent
Hafen

(10) Patent No.: US 6,548,733 B2
(45) Date of Patent: *Apr. 15, 2003

(54) FUNCTION-BASED SMALL MOLECULAR WEIGHT COMPOUND SCREENING SYSTEM IN *DROSOPHILA MELANOGASTER*

(75) Inventor: Ernst Hafen, Zürich (CH)

(73) Assignee: The Genetics Company, Inc., Zürich (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/217,694

(22) Filed: Dec. 21, 1998

(65) Prior Publication Data

US 2002/0026648 A1 Feb. 28, 2002

(51) Int. Cl.$^7$ .............................................. G01N 33/00
(52) U.S. Cl. ................................... 800/3; 800/8; 800/9
(58) Field of Search ............................ 800/3, 8, 21, 9; 536/23.1; 435/320.1; 514/1; 436/536

(56) References Cited

U.S. PATENT DOCUMENTS

| | | | |
|---|---|---|---|
| 5,593,853 A | 1/1997 | Chen et al. | |
| 5,593,862 A | 1/1997 | Hall et al. | |
| 5,639,609 A | 6/1997 | Dower et al. | |
| 5,721,099 A | 2/1998 | Still et al. | |

FOREIGN PATENT DOCUMENTS

| WO | 92/14817 | 9/1992 |
|---|---|---|
| WO | 98/03662 | 1/1998 |
| WO | 99/37672 | 7/1999 |

OTHER PUBLICATIONS

Encyclopedia Britannica On Line, 1999 Merriam–Webster, Inc., "affix.".*
Encyclopedia Britannica On Line, 1999 Merriam–Webster, Inc., "coat.".*
Aguirrezabalaga et al. Mutagenesis 9(4):341–346, Jul. 1994.*
Peloquin et al. Biotechniques 22(3):496–499, Mar. 1997.*
Dickson et al. Genetics 142(1):163–71, Jan. 1996.*
Gallant et al. Science 274(5292):1523–7, Nov. 1996.*
Gertler et al. Science 248(4957):857–60, May 1990.*
Karim et al. Genetics 143(1):315–29, May 1996.*
Kockel et al. Genes and Development 11(13):1749–58, Jul. 1997.*
Kussick et al. Oncogene 8:2791–2803, 1993.*
Lynch et al. Teratogenesis, Carcinogenesis and Mutagenesis 11:147–173, 1991.*
Kauffman, et al., 1995 Proc. Natl. Acad. Sci. USA 92: 10919–10923.
Dickson, et al., 1996 Genetics 142: 163–171.

Bishop, III, et al., 1988 Genes & Development 2: 567–577.
Thompson et al., "Modification of cell growth and longevity uisng an in vivo assay in *drosophila melangoster*." Growth 48: 86–92 (1984).
Alberts, et al., "Table 12–1" In: Molecular Biology of The Cell (2$^{nd}$ ed.), New York and London, Garland Publishing, Inc., 685–687, 1989.
Ashburnes, In: Drosophila: A Laboratory Handbook, Cold Spring Harbor Laboratory Press, 1065–1074, 1989.
Broach and Thorner, "High–throughput screening for drug discovery," *Nature* 384: 14–16, 1996.
Darling, "Mice as models of human development disorders: natural and artificial mutants," *Current Opinion in Genetics and Dev.* 6: 289–294, 1996.
Dickson, et al., "Mutations Modulating Raf Signaling in Drosophila Eye Development," *Genetics* 142: 163–171, 1996.
Dominguez and Hafen, "Genetic dissection of cell fate specification in the developing eye of Drosophila," *Cell & Dev. Bio.* 7:219–226, 1996.
Granato and Nusslein–Volhard, "Fishing for genes controlling development," *Current Opinion in Genetics and Dev.* 6: 461–468. 1996.
Gu and Singh, "Pharmacological Analysis of Heartbeat in Drosophila," *Journal of Neurobiology* 28:269–280, 1995.
van Heyningen, "Model organisms illuminate human genetics and disease," *Molecular Medicine* 3: 231–237, 1997.
Holley and Ferguson, "Fish are like flies are like frogs: conservation of dorsal–ventral patterning mechanisms," *BioEssays* 19: 281–284, 1997.
Raabe, et al., "DOS, a Novel Pleckstrin Homology Domain–Containing Protein Required for Signal Transduction between Sevenless and Ras1 in Drosophila," *Cell* 85: 911–920, 1996.
Schuler, et al., "Drosophila as a Tool for the Rapid Assessment of Chemicals for Teratogenicity," *Teratogenesis, Carcinogenesis and Mutagenesis* 2:293–301, 1982.
Schultz, et al., "The Growth and Morphogenesis of *Drosophila melanogaster* as Criteria for Screening Tests," *Cancer Res. (suppl.)* 3:86–100, 1955.

* cited by examiner

*Primary Examiner*—Deborah Crouch
*Assistant Examiner*—Joseph Woitach
(74) *Attorney, Agent, or Firm*—Ivor R. Elrifi; Kristin E. Konzak; Mintz, Levin, Cohn, Ferris, Glovsky and Popeo, P.C.

(57) ABSTRACT

A methodology for screening libraries of compounds for desirable biological/therapeutic activities, preferably using an automated system for the microinjection of compound(s) of interest into the open circulatory system (i.e., hemolymph) of Drosophila larvae genetically modified to sensitize a particular signaling pathway related to a human disease either by expression of a human disease gene or by the activation of a Drosophila gene that in the adult fly results in the development of an easily detectable phenotypes such that compounds that selectively interfere with this specific signaling pathway will modify or suppress the phenotype and can be identified rapidly and efficiently.

26 Claims, 3 Drawing Sheets

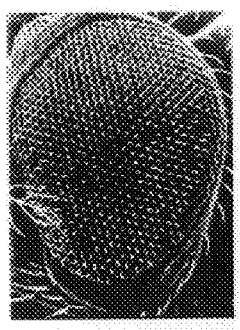 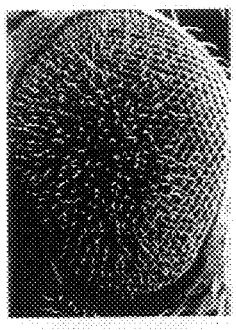 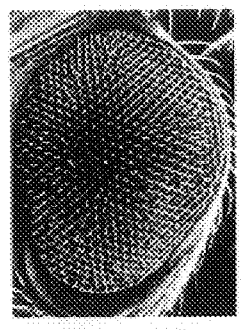 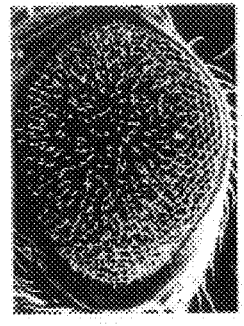
Fig. 1A  Fig. 1B  Fig. 1C  Fig. 1D
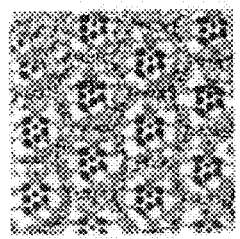 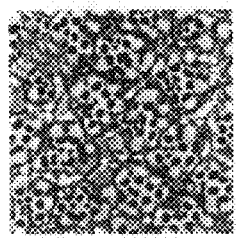 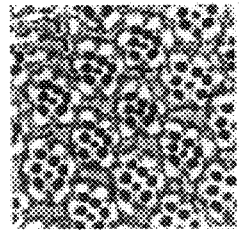 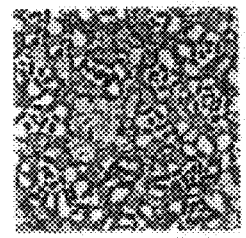
Fig. 1E  Fig. 1F  Fig. 1G  Fig. 1H

| LOCUS | ALLELE TESTED | NO. OF rafHM7; Su/+ OR rafHM7; E/+ MALES | NO. OF rafHM7; Pw+/+ MALES | RELATIVE VIABILITY (%) | MODIFICATION OF rafHM7 EYE PHENOTYPE |
|---|---|---|---|---|---|
| Su(Raf)2A | 3E8 | 73 | 136 | 54 | NONE |
|  | 4P5 | 54 | 45 | 120 | NONE |
| rolled | 2L1 | 0 | 61 | 0 | - |
|  | 6L1 | 0 | 63 | 0 | - |
| phyllopod | 3G6 | 50 | 53 | 94 | ENHANCED |
|  | 17L1 | 156 | 118 | 132 | ENHANCED |
| Su(Raf)3A | 9J1 | 0 | 83 | 0 | - |
|  | 19F2 | 0 | 60 | 0 | - |
| Su(Raf)3B | 18A2 | 0 | 174 | 0 | - |
| Su(Raf)3C | 17M1 | 127 | 121 | 105 | NONE |
| E(Raf)2A | 14O1 | 13 | 72 | 18 | ENHANCED |
|  | 16H1 | 0 | 135 | 0 | - |
|  | 16T1 | 0 | 157 | 0 | - |
| Star | 2J1 | 0 | 50 | 0 | - |

Fig. 3

FUNCTION-BASED SMALL MOLECULAR WEIGHT COMPOUND SCREENING SYSTEM IN *DROSOPHILA MELANOGASTER*

FIELD OF THE INVENTION

The present invention relates to the use of genetically-modified strains of *Drosophila melanogaster* in high-throughput screening (HTS) of small molecular weight compounds. The present invention also relates to the systematic identification of small molecules which interfere with specific disease pathways using Drosophila as the genetic model system. Additionally, the present invention relates to the use of automated screening systems employing microinjection of small molecular weight compounds, possessing putative biological activity, into the open circulatory system (i.e., the hemolymph) of genetically-modified Drosophila larva.

BACKGROUND OF THE INVENTION

The identification and subsequent characterization of new therapeutics are the primary rate limiting step in pharmacological research. Drug discovery processes are extremely lengthy. A conventional process involves the screening of thousands of individual compounds for a desired biological/therapeutic activity. Historically, less than 1 in 10,000 of the synthetic compounds have actually been approved by the Food and Drug Administration (FDA), at a cost of greater than $200 million per drug (see e.g., Ganellin, et al., 1992. In: Medicinal Chemistry for the $21^{st}$ Century. pp. 3–12 (Blackwell Publications, London, England)).

Pharmacological compounds have been sought from natural products for many years. In general, complex mixtures derived from cells, or their secondary metabolites, are screened for biological activity. Subsequently, when the desired biological activity is identified in such a complex mixture, the specific molecule which possesses the activity has been purified, using the biological activity as the means for identifying the component of the mixture which possesses the desired biological activity.

An alternative methodology for the development of novel pharmacological compounds has been to screen individual compounds which have been previously synthesized and saved in "libraries" within drug/chemical companies or research institutions. The compounds in these libraries were often initially chosen for synthesis or screening due to the fact that they possessed a particular functionality thought to be relevant to a specific biological activity.

More recently, peptide or oligonucleotide libraries have been developed which may be screened for a specific biological function (see e.g., Musser, 1992. In: Medicinal Chemistry for the $21^{st}$ Century. pp. 3–12 (Blackwell Publications, London, England); U.S. Pat. Nos. 5,593,853 and 5,639,603). For example, recombinant peptide libraries have been generated by the insertion of degenerate oligonucleotides into the genes encoding the capsid proteins of filamentous bacteriophage and the DNA-binding protein Lac I (see e.g., Cwirla, et al., 1990. Proc. Natl. Acad. Sci. U.S.A. 87:6378–6382; Cull, et al., 1992. Proc. Natl. Acad. Sci. U.S.A. 89:1865–1869 and PCT Publications Nos. WO 91/19818 and WO 93/08278). These random libraries may contain more than 109 different peptides, each fused to a larger protein sequence which is physically-linked to the genetic sequences encoding it. The libraries are subsequently screened by allowing the peptide to interact with its specific ligand (e.g., receptor, nucleic acid, etc.) via several rounds of affinity purification and the selected exposition or display vectors are then amplified in, for example, *E. coli*, and the nucleic acid contained therein is sequenced to reveal the identity of the peptide responsible for the ligand interaction.

(i) Screening Methodologies

Many of the existing therapeutics on the market to date have been identified in an accidental manner, and frequently their mechanism of action is poorly understood. A more direct approach towards the identification of new small molecular weight compounds effective against various disease conditions requires the precise knowledge of both the molecular defect underlying a given disease and the knowledge of the cellular pathways and processes in which the defective component is acting. In fact, such knowledge of the pathways involved is essential since the defective gene product may not be the best target for a small molecular weight compound. In addition, despite the great value that large libraries of molecules can have for identifying useful compounds or improving the properties of a lead compound, the difficulties of screening such libraries, particularly extremely large libraries, has limited the impact access to such libraries should have made in reducing the costs of drug discovery and development. This is, in a large part, due to the weaknesses inherent in the current screening methodologies of compound libraries which employ both cell-free and in vitro cell-based assay systems.

Currently, numerous drug screening protocols rely upon high-throughput screening (HTS) of compound libraries using cell-free or in vitro cell-based assay systems. Several drugs (e.g., cyclosporine A and mevastatin) have emerged directly from utilization of this methodology. HTS is a process by which large numbers of compounds with putative biological activity may be tested, preferably in an automated manner, for activity as inhibitors (antagonists) or activators (agonists) of a specific biological target (e.g., cell-surface receptor or a metabolic enzyme). It should be noted, however, that HTS does not actually identify a drug, but rather, the primary goal of HTS is to identify high-quality "hits" or "leads" (i.e., compounds which affect the target molecule in the desired manner) which are active at a relatively low concentration and that possess a novel structure or sequence and to supply directions for their potential optimization. Although HTS is a powerful screening tool, it possesses a number of limitations such as: (i) bioavailability; (ii) pharmacokinetics; (iii) toxicity and (iv) absolute specificity. Hence, subsequent medicinal chemical and pharmacological studies are required to convert a compound which emerges from an initial HTS screening into a therapeutically useful drug. These limitations exist because many of the properties critical to the development of a drug typically can not be directly assessed by HTS; therefore, the final compound which eventually becomes a drug is unlikely to have been the molecule present in the initial small molecular weight compound library. Generally, the greater the number and diversity of the compounds which are analyzed, the more successful the screening is likely to be, a fact which has markedly accelerated the development of HTS.

A well-designed HTS screening assay may also provide information regarding the potency of a compound of interest. Generally, the lower the concentration at which the compound of interest exhibits activity, the more likely it will exhibit specificity and, as a corollary, the less likely that it will have undesirable or deleterious side-effects. Information on specificity may also be obtained by concomitantly performing a counter-screen with a related target molecule (e.g., an HIV protease verses a cellular aspartyl protease or the serotonin 2A receptor verses the serotonin 2C receptor). Compounds which exhibit activity only against the primary target are deemed most likely to possess the necessary selectivity. If different chemotypes may be identified using the same screen, then medicinal chemists will have a broader range of options for modification of the novel, lead compound. In addition, the spectrum of compounds which score positive (and to some extent those compounds which score negative) may help to pinpoint those structural characteristics and motifs of the molecules which are responsible for their efficacy and specificity.

The HTS methodology requires four distinct elements: (i) suitably arrayed compound libraries; (ii) as assay methodology amenable to automation; (iii) a robotics workstation and (iv) a computerized system for input and analysis of incoming data from the screening assay. Currently, the 96-well microtiter plate is the standard format for automated HTS assay, although arrays of compounds on chips (see e.g., Fodor, et al., 1993. Nature 364:555–556) or on insoluble beads (see e.g., Ohlmeyer, et al., 1993. Proc. Natl. Acad. Sci. U.S.A. 90:10922–10926) have also been utilized and the assays may be performed on agar plates or other types of solid support matrices. The synthesis of combinatorial libraries may be accomplished within the 96-well microtiter plates, thereby providing addresses for the particular compounds generated by a given subset or series of reactions and thus identifying the compound of interest. Furthermore, concentrates of fermentation broths, natural product extracts or pre-existing collections of compounds (i.e., such as the repositories possessed by large pharmaceutical firms) may be dispensed in 96-well microtiter plates, either singly (simplex arrays) or as defined mixtures of 10–20 compounds per well (multiplex arrays). The later, multiplex array methodology permits a far more rapid rate of screening, but it also requires the subsequent deconvolution of the compounds within the assay mixture to identify the true active compound.

Robotics systems for HTS assays range in complexity from simple, automated dilution devices to highly evolved workstations in which multiple functions are performed by one or more mechanical arms. In the preferred embodiment of the HTS methodology, fall automation (i.e., from sample dispensing to data collection) allows for round-the-clock operation, thereby increasing the overall screening rate and mitigating the potential for human error common in highly redundant procedures such as HTS. Given the variety of libraries which are currently available, the large number of compounds present in each library and the need to compare the results obtained from different screening assays, data collection and management are critical to automated HTS. Databases of structural characteristics, assays performed, screening results and the like, must be relational (i.e., interlinked) so as to allow the necessary information to be extracted by a query from any perspective. Hence, one should be able to search, for example, for all compounds which are active at a certain threshold concentration in a particular screen, or for the characteristics of all compounds of similar structure in different screens.

Although any standard drug activity assay may, in theory, be performed utilizing a HTS methodology, the conversion to a fully automated process imposes certain, frequently formidable, constraints which affect the design of the assay in practice. Procedures which are routine when performed on the bench (e.g., centrifugation to remove cellular debris or to collect the beads, rinsing of the wells in the microtiter plate during an ELISA-based assay and the like) are often extremely difficult to automate. The greater the number of steps required in the assay, the greater the difficulty in developing automation. The ideal HTS assay is one in which all required manipulations may be performed in a single well of the microtiter plate.

Current screening methodologies of compound libraries employ both cell-free and in vitro cell-based assay systems, although each of these aforementioned systems possesses intrinsic limitations and weaknesses. For example, in the case of the cell-free systems, screening is limited to single candidate target molecules. Such putative targets are generally identified upon the basis of enzymatic activity (e.g., kinases) or specific protein domains involved in protein-protein interaction (e.g., src-homology 2 (SH2) domains) (see e.g., Broach, et al., 1996. Nature 384:14–16). Another potential limitation of the cell-free assay systems is that they do not provide an inherent test for either the specificity of the interaction, nor of the toxicity of the particular compound. In addition, the prime drug target for a given disease condition is ideally the weakest point within the signaling chain. Cell-free systems do not permit the identification of such targets, as signaling pathways are made up of combination of cell membrane, cytoplasmic, and nuclear-based components whose complex interactions are disrupted in cell-free systems.

In contrast, cell-based assays have several notable advantages over cell-free systems. First, the starting material (the cell) is self-replicating, thus avoiding the investment involved in the preparation of a purified target, in chemically-modifying the target to suit the specific type of screening assay, and the like. Second, the targets and readouts are examined in a biological context which (hopefully) mimics the normal physiological conditions present in vivo. Third, cell-based assay systems can provide insights regarding bioavailability (i.e., the compound must enter the cell to affect an intracellular target) and cytotoxicity (whether a compound compromises cellular processes and growth). However, while in vitro cell-based assays more closely model a compound's specificity, toxicity or possible mode of action within a cell, they often provide inadequate similarity to the in vivo disease condition, as most diseases develop within multicellular tissues. The results in a cell-based system are limited to such criteria as changes in the mitotic rate or reporter gene expression. Nonetheless, cell-based systems are becoming more frequently utilized as an alternative to in vitro biochemical assays for HTS.

Generally, such in vitro cell-based assays require the ability to examine a specific cellular process and a means to measure its output. For example, agonist-mediated activation of a cell-surface receptor or a ligand-gated ion channel may be followed by monitoring its coupled cellular response (see e.g., Levitzki, 1996. Curr. Opin. Cell Biol. 8:239–244). Although the immediate downstream event (e.g., transient elevation in intracellular $CA^{2+}$ levels, phosphorylation of target proteins and the like) may be difficult to evaluate in a quantitative automated format, the subsequent transcriptional changes may be more amenable to such monitoring. For example, binding of isoproterenol to the β-adrenergic receptor elicits a transient rise in cyclic AMP (cAMP) levels, activating protein kinase A (PKA), which translocates to the nucleus and phosphorylates a transcription factor (CREB) which subsequently recognize cAMP response elements (CREs). Accordingly, CREB activation may be detected and quantified by measuring the expression level of a reporter gene whose transcription is driven by an enhancer element containing CREs (see e.g., Kee, et al., 1996. J. Biol. Chem. 271:2373–2375). Enhancer elements which couple gene expression to distinct signal transduction pathways have now been characterized (see e.g., Treisman, 1996. Curr. Opin. Cell Biol. 8:205–215) and reporter genes which generate products that can be readily adapted to the HTS format are also currently available and include, but are not limited to: β-galactosidase, luciferase, alkaline phosphatase, β-lactamase and the green fluorescent protein O(jellyfish).

(ii) Utilization of Drosophila Melanogaster as a Model System for the Genetic Dissection of Cellular Processes The fruitfly, Drosophila melanogaster, has been used as an ubiquitous model for the characterization of cellular processes (e.g., signaling pathways) involved in a variety of human diseases. In fact, the cellular functions of many genes known to be affected in human diseases were initially identified in Drosophila (see e.g., Holley, et al., 1997. Bioassays 19: 218–284). This high degree of conservation of morphogenetic processes between Drosophila and humans has made Drosophila a prime model system for the identification of putative drug targets using function based genetic approaches. Homeotic genes constitute one of the best-known examples of genes first identified in Drosophila that have provided insight into the mechanisms of human development and disease (see e.g., van Heyningen, 1997. Mol. Med. 3:231–237).

Drosophila eye development is a prime example of a model system for the study of well defined and functionally integrated genetic controls. Drosophila eye development has provided most of the important genetic information regarding evolutionarily conserved mechanisms. One of the earliest transcriptional regulatory regions controlling Drosophila eye development, the PAX6 gene, was initially defined in humans and the mouse as, respectively, the gene mutated in aniridia (absence of the iris; see e.g., Ton, et al., 1991. Cell 67:1059–1074) and in Small Eye strains (see e.g., Hill, et al., 1991. Nature 354:522–525). Subsequently, it was discovered that a Drosophila homologue existed that mapped to the eyeless locus, and that the homolog was functionally disrupted by transposon insertion in eyeless fruitflies (see e.g., Quiring, et al., 1994. Science 265:785–789). Another novel finding involving carefully controlled ectopic expression of either the fly PAX6 gene or the mouse homologue in different Drosophila imaginal disks was shown to lead to the development of relatively "normal" eyes and antennae (see e.g., Halder, et al., 1995. Science 267:1788–1792). This high degree of conservation of both gene sequence and function, across a broad phylogenetic spectrum, has served as a major incentive for a reaffirmation of the concept of wide-ranging evolutionary gene conservation (see e.g., Banfi, et al., 1996. Nat. Genet. 13:167–174).

While the concept of wide-ranging evolutionary gene conservation is not new, it has been critical in the elucidation of many complexities in, for example, the Ras and tyrosine kinase signaling pathways via the analysis of Drosophila eye mutants. These genes encode components of a highly conserved signaling cascade which has in part been described in vertebrate cells. Activation of the sev (sevenless) receptor by boss (bride of sevenless) presumably results in receptor dimerization and subsequent autophosphorylation on tyrosine residues. This autophosphorylation creates binding sites for the Drk SH2/ SH3 adaptor protein (see e.g., Raabe, et al., 1995. EMBO J 14:2509–2518). Drk binds to sev via its SH2 domain and to the C-terminus of Sos via its SH3 domains and thereby brings the Sos protein to the membrane. Sos is a guanine nucleotide releasing factor that activates Ras1 by facilitating the conversion from GDP-Ras1 to GTP-Ras1. Ras1 in turn activates a cascade of three cytoplasmic kinases: homologs of Raf, MEK (MAPK kinase) and MAP kinase encoded by the genes raf, Dsor1, and rolled, respectively (Dickson, et al., 1996 Genetics 142:163–171). All of these cytoplasmic components are also required for signaling by other RTKs in Drosophila, including both torso and DER (see e.g., Chang, et al., 1994. Cold Spring Harbor Symp. Quant. Biol. 59:219–226; Dominguez & Hafen, 1996. Drosophila Sem. Cell Dev. Biol. 7:219–226). The elucidation of these signaling pathways are of great importance as they control various aspects of human developmental regulation, hormone action, and neoplasia.

Genetically manipulated Drosophila have served as a powerful tool for dissecting and characterizing gene pathways. Recombinant methodologies used to modify specific Drosophila genes are well known in the art, as are methodologies used for the maintenance of said Drosophila strains, said strains being homozygous, hemizygous, or heterozygous for defined allelic combinations of the gene or genes of interest. One such phenotype is an irregular, rough eye surface induced upon activation of a genetically modified raf gene in the Ras signaling pathway. In such a genetically sensitized background, mutations in genes coding for rate limiting components in a particular signaling pathway can be identified as modifiers of the phenotype (see e.g., Dickson, et al., 1996. Genetics 142:163–171). These mutations thus identify gene products whose activity or function is critical for the development the disease-related phenotype.

Extensive genetic screens for mutations in genes involved in the transduction of the signal from the activated receptors to the nucleus have revealed an evolutionarily conserved signaling cascade that is used by the different receptors to elicit diverse cellular responses. The components of the signaling pathways between Drosophila and humans are highly conserved. Inhibitors developed against human proteins also block the function of Drosophila proteins. For example, the immunosuppressant drug rapamycin has been shown to block the activation of ribosomal protein S6 kinase (S6K) in mammalian and Drosophila cells.

The Drosophila compound eye has been used extensively for the systematic genetic dissection of conserved signaling pathways. Its structure and usefulness in characterization of signaling pathways is therefore discussed in some detail. The Drosophila compound eye is composed of a hexagonal array of approximately 800 identical units, called ommatidia. Each of these units consists of eight photoreceptor cells (R1–R8), four lens-secreting cone cells, and pigment cells that optically insulate each ommatidium. This highly organized structure develops from a single layer epithelial sheet, the eye imaginal disc, during larval and pupal stages by the stepwise recruitment of cells into the ommatidial clusters. During this process, differentiating cells specify the fate of neighboring, but still undetermined, cells by inductive signals.

As previously discussed, a variety of cell-fate decisions are controlled by the activation of receptor tyrosine kinases (RTKs). One such interaction involves the Drosophila rough eye phenotype which is an irregular, rough eye surface induced upon activation of a genetically-modified raf gene (a downstream effector of the Ras1 oncogene) in the Ras signaling pathway (see e.g., Dickson, et al., 1996. Genetics 142:163–171). In such a genetically-sensitized background, mutations in genes encoding rate limiting components in a particular signaling pathway may be identified as modifiers of the phenotype. These mutations thus identify gene products whose activity or function is critical for the development the disease-related phenotype.

Another function of RTK involves the control of R7 photoreceptor cells during the development of the compound eye of Drosophila. The inductive signal specifying the fate of the R7 cell is well-understood since mutations in two genes, sevenless (sev) and bride of sevenless (boss), specifically block the specification of the R7 precursor as a photoreceptor cell giving rise to ommatidia which contain seven instead of eight photoreceptors. The boss gene encodes a membrane protein that is exclusively expressed on the surface of the R8 cell at the time when the presumptive R7 photoreceptor cell is recruited into the cluster. The sev gene encodes a receptor tyrosine kinase expressed in a subpopulation of cells within the ommatidial clusters including the R7 precursor and the four cone-cell precursors. The boss protein binds to and activates the sev receptor on the neighboring R7 precursor and, in the absence of either boss or sev function, the R7 precursor fails to initiate neuronal differentiation and instead develops as a non-neuronal cone cell. Expression of constitutively activated forms of sev or the ubiquitous expression of the boss gene showed that sev activation is sufficient to specify the R7 fate not only in the R7 precursor cell but also in the four cone-cell precursors. As illustrated in FIG. 1, during the development of each ommatidial unit, five cells, collectively referred to as the R7 equivalence group, are competent to choose between two alternative fates: the neuronal photoreceptor fate when sev is active and the non-neuronal cone cell fate when sev is inactive.

The formation of R7 photoreceptor cells is a model system where scientists have a complete knowledge of all genes acting in the signal transmission pathway that extends from the cell membrane to the nucleus (see e.g., Dominguez, et al., 1997. Dev. Biol. 7:219–226). Although extensive genetic screens for recessive, viable mutations affecting the development of the R7 cells have been carried out, mutations in only four genes apart from sev and boss have been identified. Flies homozygous for mutations in the sina gene (which encodes a nuclear protein) lack R7 cells and are non-viable. Mutations in Gap1 (encoding a homolog of a GTPase activating protein), yan (encoding a transcription factor of the ETS-family) and tramtrack (ttk) have been shown to cause the formation of multiple R7 cells in each ommatidium (see e.g., Dominguez, et al., 1997. Dev. Biol. 7:219–226). These results tends to suggest that Gap1, yan and ttk act as inhibitors of the R7 specification; whereas sina acts as an activator.

Mutations in genes whose products are also involved in other developmental decisions prior to the formation of the eye may cause less informative phenotypes such as lethality so that their role in R7 development cannot be tested directly and alternative genetic strategies are thus required to identify them. The most successful approach to date has been pioneered by Simon et al. (1991, Cell 67:701–716) and focuses on the development of the R7 cell. In this study, researchers utilized a hypomorphic sev mutation which encoded a partially functional, temperature-sensitive sev receptor which, at an intermediate temperature, provides barely sufficient activity to specify R7 cells. In this background, a 50% reduction in the amounts of an essential, rate-limiting component due to the inactivation of one gene copy by a mutation was demonstrated to prevent the formation of R7 cells. In this sensitized genetic background, normally recessive mutations thus acted dominantly in the R7 decision. A similar, genetically-sensitized system was also provided by the multiple R7 phenotype in sev gain of function (GOF) mutations (sev$^{GOF}$). In this assay, the overall number of cells of the R7 equivalence group which assume R7 cell fate provide a sensitive measure of the sev kinase activity and, additionally, of the efficiency with which the signal is transduced. The recruitment of extra R7 cells disrupts the hexagonal array of the ommatidial units and causes a roughening of the external surface of the eye. Mutations that reduce the efficiency of sev signaling are thus detected as suppressors of the rough eye phenotype of sev$^{GOF27}$. It is by the utilization of such simple and reliable F1 screens that many of the genes for cytoplasmic signaling components involved in sev signal transduction have been discovered.

The value of Drosophila as a screening system for evaluating the biological activities of chemicals has been well-documented (see e.g., Schulz, et al., 1955. Cancer Res. 3(suppl.): 86–100; Schuler, et al., 1982. Terat. Carcin. Mutag. 2:293–301). Small numbers of chemical substances are administered to larvae or flies by feeding, and flies are then analyzed for survival and for phenotypic alterations. Although these conventional tests show the potential use of Drosophila as a tool to analyze the function of small molecular weight compounds, these methods neither permit high-throughput screens, nor permit the directed search for small molecular weight compounds that interfere with a specific morphogenetic pathway related to a human disease condition. Application of compounds by feeding requires relatively large amounts of the substance, and its uptake by the larvae and thus its final concentration is, at best, difficult to control. Furthermore, application by feeding does not permit automation of the procedure necessary for high-throughput analysis.

The principal property required of a small molecular weight compound screen is that distinct mechanisms of induction produce different outcomes. Response patterns can thus be used to group drugs with similar mechanisms and hence identify novel activities. To be successful, such patterns have to be relatively insensitive to potency, so that agents with the same mechanism but different potency are classed together. The principle to be exploited is that the differences in the panel cells' capacities to respond depend on the components and assembly of their signal transduction and effector mechanisms for differentiation. With the current screens using cell-free or in vitro cell-based assays, these differentiation end-points are difficult to assess and cell number or cell mass may be the more appropriate assay for their high-throughput designs. This is due to the fact that current screening methodologies can not easily discriminate growth arrest due to differentiation from other antiproliferative or simple cytotoxic effects (see e.g., Francis, et al., 1994. Differentiation 57:63–75).

Whole embryo cultures have also been used to screen for chemical effects in, for example, rodents and chickens. Adverse embryonic outcomes (malformations or embryotoxicity) are directly related to the serum concentration of the compound being tested. These serum concentrations can be directly compared to the serum concentration in the human. Whole embryo culture systems are problematic in that they result in large numbers of in vivo false-positives, and development within the cultures is limited to the very early stages of embryogenesis (see e.g., Webster, et al., 1997. Int. J. Dev. Biol. 41:329–335). Similarly, the nematode *Caenorhabditis elegans* is frequently utilized as a model organism for the genetic dissection of developmental controls and cell signaling. However, in *C. elegans* there are no genetically sensitized systems available that permit reliable detection of even a two-fold reduction in a signaling process caused by either a chemical compound or a mutation in a gene. Although *C. elegans* can be grown in microtiter plates, the phenotypic screens are markedly limited. Also, chemical compounds would necessarily be administered by feeding, and would thus possess all of the aforementioned inherent disadvantages.

Another widely-utilized model genetic system is yeast. Although yeast are easily maintained and can readily be grown in large numbers, they are a simple, single-celled organism and thus possess the inherent limitation of being incapable of replicating a complex, multi-cellular system. Although the yeast system offers a comparatively higher throughput, its possesses inherent limitations, as most disease conditions are dependent upon cell-cell interactions within tissues that cannot be modeled in yeast. Finally, and most importantly, the overall degree of conservation of signaling pathways between yeast and human is significantly lower than that between Drosophila and humans.

Accordingly, there remains an as yet unfulfilled need within the relevant fields for a rapid, quantitative HTS screening methodology which has the ability to be fully automated and that utilizes a genetic model possessing, but not be limited to, the following characteristics: (i) a high degree of conservation of the various signaling pathways involved in the etiology of human disease; (ii) the ability to be grown rapidly in large numbers with little effort; (iii) a stable genetic mutation(s) and (iv) an easily discernible genetic outcome for use in the screening procedure.

SUMMARY OF THE INVENTION

The present invention targets the ubiquitous nature of the signaling pathways present in most every cell and couples them to an assay system of choice within the appropriately modified Drosophila strain. More specifically, the present invention utilizes genetically sensitized Drosophila strains which possess mutations within a selected signaling pathway in the construction of a high-throughput screen (HTS) of small molecular weight compounds to facilitate the identification and characterization of novel, lead drug candidates which dominantly modify the phenotypic effects of these aforementioned sensitized Drosophila signaling pathways.

The present invention discloses a methodology for the screening of compounds for desirable biological/therapeutic activities which involves the screening of individual chemical compounds which have been synthesized and cataloged in libraries of drug or chemical companies or research institutes. The active "lead" compounds and novel chemical entities identified and characterized by the present invention may be utilized for the development of bioactive "leads" in small molecule libraries for pharmaceuticals, agrochemicals and the like.

The high degree of conservation of morphogenetic processes between Drosophila and humans has made Drosophila a prime model system for the identification of new putative drug targets using function-based genetic approaches. Genetically sensitized Drosophila systems, wherein the gene modification results in a dose-sensitive phenotype, permit detection of a mere two-fold effect of small compounds on specific signaling pathways related to human diseases. It is preferred that such Drosophila strains are genotypic (+/null), and hence are hemizygous for a dose sensitive gene within a given signaling pathway.

The present invention is a novel combination of an automated, in vitro HTS assay with an in vivo "readout" system comprised of *Drosophila melanogaster* which are genetically-sensitized for a specific disease pathway, preferably a human disease pathway. Hence, the present invention discloses a methodology which serves to "bridge the gap" of the presently-utilized screening systems by use of a well-established model for human disease (Drosophila) for the screening of large numbers of compounds for biological/therapeutic activity in a rapid, quantitative and highly efficacious manner. The expression of human disease genes or their homologs within the developing Drosophila larva models the effects of these genes in human cells and subsequently produces the phenotypes which are modified by either the mutations within these interacting genes, or by compounds which block the function of the corresponding gene product. These gene products are prime candidates as targets for small compounds which interfere with their function.

The preferred embodiment of the present invention employs an automated system for the microinjection of compound(s) of interest into the open circulatory system (i.e., hemolymph) of Drosophila larvae, most preferably of Drosophila third instar larvae, that have been previously genetically-modified in a gene specific to a signaling pathway involved in human disease. More preferably the modified gene is involved in the Ras signaling pathway and has a functional phenotype that is readily scorable by observation of the developing Drosophila eye. However, it is contemplated that the invention can use any signaling pathway to monitor phenotypic changes involved in the development of any imaginal disk. Following maturation of the microinjected Drosophila larvae, the biological effect of the injected compound(s) are assessed in adult flies. In addition, the screening methodology disclosed by the present invention allows the simultaneous observation of: (i) the general biological toxicity of the microinjected compound(s) through 50% lethal dose (LD50) computations: (ii) the specificity of the modification of the specific Drosophila phenotype (i.e., suppression of the rough eye phenotype) and (iii) the non-specific interference with other well-defined developmental and physiological pathways.

BRIEF DESCRIPTION OF THE DRAWINGS

FIG. 1 is a series of scanning electron micrographs of the Drosophila compound eye (Panels A–D) and light micrographs of tangential cross-sections of the Drosophila compound eye (Panels E–H) following genetic modification of the $Raf^{torY9}$ phenotype by Su(Raf) and two E(Raf) mutations. Panels A and E illustrate the wild-type genotype; Panels B and F illustrate the $Raf^{torY9}$/+genotype; Panels C and G illustrate the $Raf^{torY9}$/+:Su(Raf)3A$^{9J1}$ genotype and Panels D and H illustrate the $Raf^{Y9}$/+, +/E(Raf)2A$^{16T1}$ genotype. It should be noted that the Su(Raf) and two E(Raf) mutations dominantly-modify the overall degree of Drosophila compound eye texture roughening in $Raf^{torY9}$ flies. In contrast, in the case of Su(Raf)3A, all ectopic R7 cells were eliminated and the eye regained the smooth texture observed in wild-type Drosophila.

FIG. 3 illustrates the genetic interactions between $raf^{HM7}$ and Su(raf) and two E(Raf)loci. For viable combinations following mating, the eyes of both classes were compared for any modification of the mild degree of roughening caused by the $raf^{HM7}$ mutation, alone. Genetic interactions between $raf^{HM7}$ and Su(Raf) and E(Raf) loci were analyzed as follows. $raf^{HM7}$, $w^a$/FM7 virgins were mated to Su(Raf)/$Pw^+$ or E(Raf)/$PW^+$ males and the total number of $raf^{HM7}$ progeny surviving to adulthood scored for each class. For viable combinations, the eyes of both classes compared for any modification of the mild roughening caused by the $raf^{HM7}$ mutation.

DETAILED DESCRIPTION OF THE INVENTION

Figure 2:
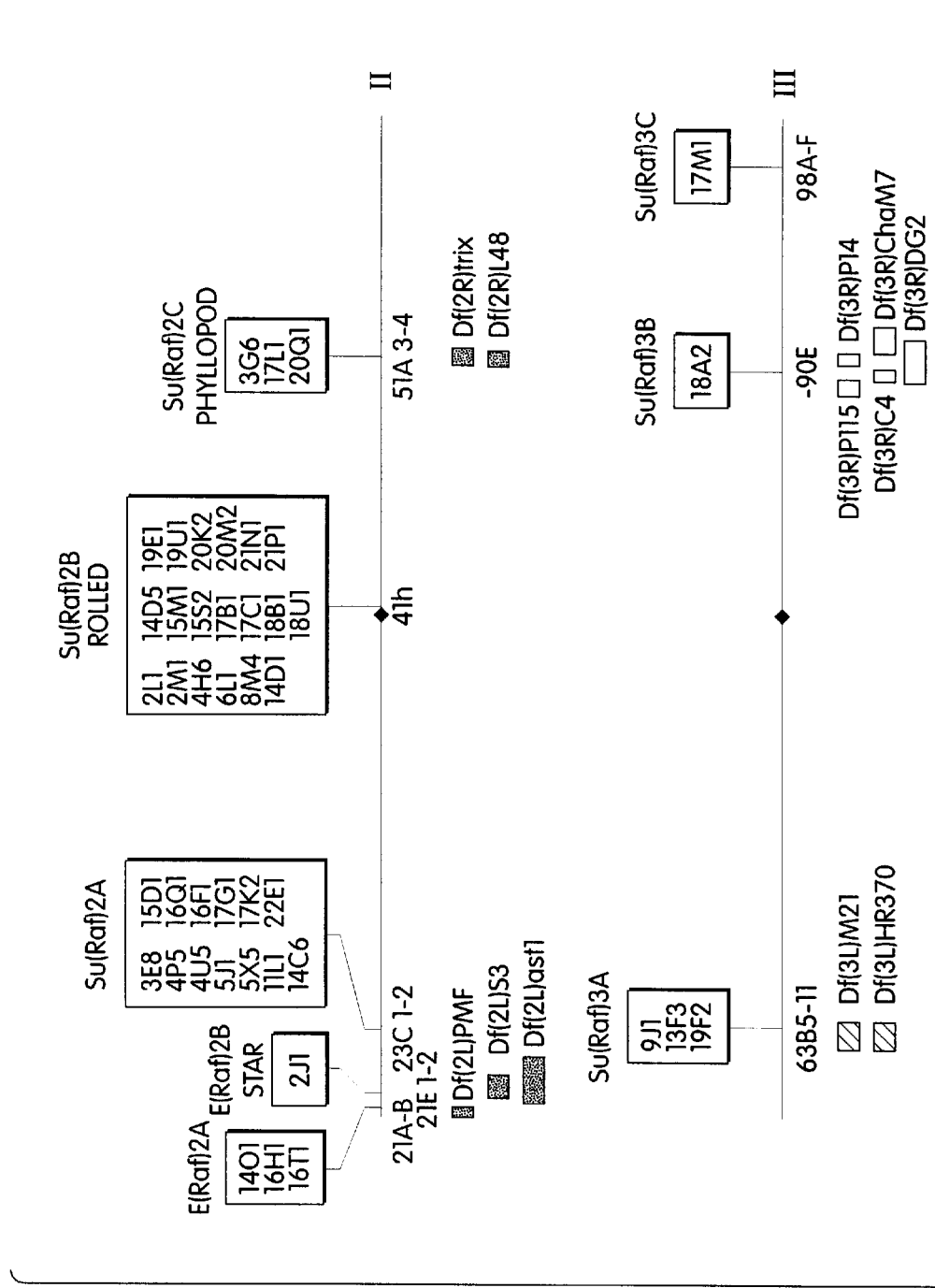
FIG. 2 is a schematic illustration of the known or estimated cytological chromosomal locations of all six Su(Raf) and two E(Raf) complementation groups (loci). All loci were mapped to either chromosome 2 or 3. In addition, the approximate chromosomal breakpoints of selected deficiencies are also shown. Deficiencies which both modified the $Raf^{torY9}$ phenotype and failed to complement EMS-induced Su(Raf) and two E(Raf) mutations are indicated by the solid black box (■). The two deficiencies which failed to complement Su(Raf)3A but did not appreciably suppress $Raf^{torY9}$ are indicated by the lightly-shaded box (□). The deficiencies completely spanning the interval to which Su(Raf)3A was mapped, but which failed to modify either the $Raf^{torY9}$ phenotype or display an obvious phenotype in trans to Su(Raf)3A$^{1842}$ are indicated by the non-shaded box (□).

The present invention provides an efficient methodology for the quantitative, systematic identification of small molecular weight molecules which interfere with specific disease conditions in an animal model system. As previously discussed, genetically-modified stains of the fruitfly, *Drosophila melanogaster*, have played a pivotal role in the identification of new genes whose products act in signaling pathways which are altered in human diseases (see e.g., Dickson, et al., 1996. Genetics 142:163–171; Dominguez, et al., 1996. Dev. Biol. 7:219–226). Such genetically sensitive backgrounds have been used previously to identify mutations in genes coding for rate limiting components in a particular signaling pathway. The present invention makes use of these aforementioned genetically-modified Drosophila strains to screen small molecular weight compounds of interest for biological activity which functions to interfere with specific disease-related pathways.

High-throughput screening (HTS) of collections of chemically-synthesized molecules and of natural products (such as microbial fermentation broths) has traditionally played a central role in the search for lead compounds for the development of new pharmacological agents. Moreover, the potent and specific biological activities of many low molecular weight peptides make these molecules attractive starting points for therapeutic drug discovery (see e.g., Hirschmann, et al., 1991. Angew. Chem. Int. Ed. Engl. 30:1278–1301). The present invention discloses a methodology for the screening of compounds for desirable biological/therapeutic activities which involves the screening of individual chemical compounds which have been synthesized and cataloged in libraries of drug or chemical companies or research institutes. The active "lead" compounds and novel chemical entities identified and characterized by the present invention may be utilized for the development of bioactive "leads" in small molecule libraries for pharmaceuticals, agrochemicals and the like.

With respect to the generation of the small molecular weight compound libraries of the present invention, the combination of biochemical diversity is often synergistic with the metabolic diversity obtained from the in vivo production of "natural products". Collections of naturally or synthetically produced chemical or oligomeric compounds, for example peptides, can be administered to cultures of microorganisms. In accord, each microbial strain may potentially create numerous modified chemical derivatives, thus generating a "metabolite library". Because each of these aforementioned cultures would (potentially) contain a very complex mixture of metabolites, a highly efficacious method of screening would be required (i.e., HTS). An aliquot of the library is incubated with each of the many strains typical of a microorganism fermentation screening program, and the media screened utilizing an HTS-based assay. In another aspect of the invention, natural product diversity is screened by creating a mixture of combinatorially-tagged liposomes; wherein each liposome preferable encapsulates only one member or a simple mixture of a natural product compound library. The libraries which are generated by the methodologies disclosed herein may be screened for any biological activity known within the art. These include, but are not limited to: anti-microbial activity, anti-tumor activity, enzyme inhibiting activity, receptor binding, growth promotion activity, and in vitro and in vivo tests for biological responses.

With the advent of genomics, combinatorial paradigms and high-throughput screening (HTS) assay-based pharmacological testing, the number of compounds possessing biological/therapeutic activity is likely to markedly increase. HTS assays are, preferably, based upon automation, validation and integration of in vitro absorption-metabolism models and database management (see e.g., Rodrigues, et al., 1997. Phaim. Res. 14:1504–1510). Complementary to this tenet is the need to generate a taxonomy of known compounds, identifying those with similar mechanisms, preferably in a way that provides clues as to the nature of those mechanism.

The present invention discloses a screening methodology which is based upon the utilization of genetically-sensitized Drosophila systems with a new method for drug administration which permits both high-throughput and automation. Based upon previous experience with genetic screens for dominant modifier mutations, genetically-sensitized systems comprising specific pathways which are sensitive to such modifier mutations will permit detection of mere two-fold effects of small molecular weight compounds on specific signaling pathways related to human diseases. This assay sensitivity results from the ability to differentiate dose-dependent phenotypes of the modified Drosophila related to the presence of none, one, or two modified alleles within its genome. The methodology disclosed by the present invention is both more powerful and more sensitive than traditional, cell-free or in vitro cell-based assay systems. In addition, the Drosophila-based screening assay disclosed herein is based upon a biological "readout" related to human disease, and its intrinsic ability to test for both the overall specificity and toxicity of a compound(s) of interest.

It is contemplated that any signaling pathway may be utilized in the present invention. Many, if not all, signaling pathways are present in every living cell. However, only a subset of pathways are active at any given time in development. The present invention would deliver small molecule compounds to be tested at the time of development when the activity of the desired pathway is required. In Drosophila, the most sensitive phenotypic changes occur in the developing imaginal disks in the third instar larva, as most differentiation occurs at this stage.

As previously discussed, signaling pathways which play an important role in human diseases are the "targets" of this screening assay. Many, if not all, intracellular signaling pathways are indigenous to every cell. However, only a small subset are biologically active at any given time during cellular development and differentiation. Additionally, cell specificity is conferred upon activation of a specific signaling pathway by effector genes located downstream of a given pathway. It is these downstream effector genes which determines the cell- or tissue-specific phenotype, even though the signaling pathway may actually be indigenous to all cells. These signaling pathways may utilized intracellular "signals" which are normally turned on within the cells of interest, or they may utilize ectopic pathways. Ectopic expression of a component of a given pathway may be induced during development in either a temporally or spatially restricted manner. If the intact signaling pathway to be targeted is present within a cell which ectopically expresses the induced component, the component will activate the targeted signal transduction pathway. The prime target of a signaling pathway is ideally the component which is the most sensitive to alterations within the signaling pathway. The assay methodology of the present invention relies upon the screening of small molecular weight compounds to identify lead compounds that modify essential components in a given signaling pathway, resulting in an observably altered phenotype in comparison to untreated, wild-type Drosophila.

One experimental approach for the identification of new components of any given biological process is to search for mutations which dominantly modify the effects of another mutation disrupting the same biological process. This technique allows these aforementioned mutations to be recovered in a simple one-generation ($F_1$) screening assay. More importantly, by sensitizing only a single biological pathway, one may create conditions in which even a slight reduction of gene activity (e.g., due to the loss of only one functional copy of the gene) can result in a detectable phenotype. This is of particular utility when the gene is involved in many other cellular processes, and a more severe loss of function may therefore produce an experimentally less-informative phenotype (e.g., such as lethality). This approach has been successfully used to identify components of the sevenless (sev) RTK signal transduction pathway involved in the induction of the R7 fate during eye development (see e.g., Simon, et al., 1991. Cell 67:701–716).

The preferred embodiment of the present invention comprises the use of Drosophila strains which are genetically-modified within the Ras proto-oncogene signaling pathway. A component of this pathway, the Raf serine/threonine kinase, has been demonstrated to play a critical role in the signal transduction pathways activated by receptor tyrosine kinases (RTKs) across a broad phylogenetic spectrum. Within these signaling pathways, Raf acts to couple Ras activation to the mitogen-activated protein kinase (MAPK) cascade, which consists of the protein kinases MEK (MAPK kinase) and MAPK (see e.g., Marshall, 1995. Cell 80:179–185). The roles of these proteins in Raf signaling have been well-established by both biochemical and genetic studies. Less well-understood, however, are the roles of other Raf-binding proteins such as 14-3-3 proteins (see e.g., Fanti, et al., 1992. Nature 371:612–614; Freed, et al., 1994. Science 265:1713–1716; Fu, et al., 1994. Science 266:126–129), hsp90 (see e.g., Stancato, et al., 1993. J. Biol. Chem. 268:21711–21716) and immunophilins (see e.g., Stancato, et al., 1994. J. Biol. Chem. 269:22157–22161), as well as the overall extent to which signal transduction via Raf is further regulated by as yet uncharacterized proteins acting within this, or parallel signaling pathways.

In genetically modified Drosophila strains, specific signaling pathways involved in human diseases can be activated at a threshold to produce an easily detectable altered phenotype. It is preferred that such strains are genotypic (+/null), and hence are hemizygous for a dose sensitive gene within a given signaling pathway. These gene products are prime candidates as targets for small compounds that interfere with their function.

Activation of the Ras/MAP kinase cascade by Torso RTK results in the specification of head and tail regions in embryonic cells while activation of the same cascade by the sev RTK in the developing eye results in the specification of photoreceptor cell fate. It is possible that each of these receptors activates specific pathways in addition to the common Ras/MAP kinase pathway. The cell-type specific response may depend on which of these parallel pathway is activated by a given receptor. In vertebrate cell culture systems, it has for example been shown that the platelet derived growth factor (PDGF) receptor activates multiple signaling pathways. Identification of the general signaling components downstream of sev, namely Torso and DER (Drosophila homolog of the EGF (epidermal growth factor) receptor), is based on the study of loss-of-function (LOF) mutations, and indicate that the corresponding gene products thus identified are necessary for signaling. Indeed the complete removal of Drk, Sos, or Ras1 function in the Torso pathway produces a less severe phenotype than removal of either Torso or Raf function. This suggests that Torso can activate Raf independently of Drk, Sos and Ras1.

Additionally, Drosophila possessing the rolled gain of function mutation Sevenmaker ($rl^{SEM}$) display a number of additional phenotypes that resemble those of gain of function mutations in torso and DER. Embryos derived from $rl^{SEM}$ females resemble those produced by females carrying a weak torso$^{GOF}$ mutation since they lack to a variable degree the central segmented region. Similarly, the formation of extra veins on the wing of $rl^{SEM}$ flies is reminiscent of the Elp phenotype caused by a gain of function mutation in DER. Therefore, hyperactivation of MAP kinase is not only sufficient to activate the sev pathway but also the developmental pathways controlled by other RTKs.

The activation of RTK-specific signaling pathways that act in parallel to the general Ras/MAP kinase pathway is a possible way of maintaining the specificity of the inducing signal from the receptor to the nucleus. The decision of how a cell responds to the generic signal is taken in the nucleus and the nature of the response is determined to a large extent by the combination of nuclear factors present in the different cells at the time of induction. Hence, it may be an evolutionary advantage to use the same universal signaling cascade which can be activated by a number of different cell surface receptors to elicit a limited set of responses at any given stage in development and thereby successively restrict the developmental potential of cells.

It will be readily apparent to those individuals skilled in the art that other genetically-modified Drosophila strains may be used in the practice of the present invention. An important attribute in choosing other appropriate Drosophila strains is that the strains have an easily monitored phenotype which is detectably-altered in response to the modification of genes related to disease pathways. Appropriate disease pathways include, but are not limited to, signaling pathways controlled by the Ras proto-oncogene; the WNT tumor suppressor gene; Rb (retinoblastoma tumor suppressor gene); HH (hedgehog development regulator) or the HH vertebrate homolog SHH (sonic hedgehog developmental regulator); activated protein kinase B (PKB/AKT); insulin receptor; insulin receptor substrates (IRS); c-src proto-oncogene; c-Jun proto-oncogene; c-myc proto-oncogene; p53; Janus kinases (JAK/STAT pathway); nitric oxide (NO); calmodulin; cAMP dependent protein kinase (PKA); $Ca^{2+}$ dependent protein kinase (PKC); growth factors such as GH, TGF, PDGF and the like; receptor tyrosine kinases (RTKs); interferons (IFN); lipid metabolites; steroid hormones; phosphatidylinositol; G-protein coupled receptors; c-abl proto-oncogene; TGF-β and Smad gene family members; interleukins; GTPases; and ionophores. This list has been provided by way of example, for purposes of illustration only, and is not intended to be limiting with respect to scope, either real or implied.

The present invention discloses a methodology for the screening of genetically-modified Drosophila systems which are sensitive to gene dosage. The Drosophila phenotype which is to be assayed may involve the development of the eye, wing, or any other structure that develops from the imaginal discs in the fly. It should be noted that all previous assays to test the role of small molecular weight compounds have been performed with non-genetically-modified, wild-type Drosophila. Small molecular weight compounds will be administered by microinjection into the open circulatory system (i.e., hemolymph) of genetically-modified Drosophila third instar larvae for subsequent use in high-throughput screening (HTS) assays of small molecular weight compound libraries and/or in the identification of the dose response curve (or other pharmacological parameters) of lead compounds of interest.

The Drosophila third instar larval stage was chosen for both practical as well as specific considerations, which include, but are not limited to: (i) the third instar larvae are easily manipulated at this stage of development; (ii) the third instar larvae are large enough to facilitate automated microinjection in a high-throughput screening (HTS) assay; (iii) third instar larvae have an open circulatory system (i.e., hemolymph) through which there is rapid diffusion of the administered compound of interest; and (iv) in the third instar larvae myriad cellular signaling pathways are active in the growth and patterning of imaginal discs, which give rise to the adult structure(s). At this stage any one of these pathways can be genetically sensitized in a way that small perturbation in its activity lead to readily detectable phenotypes in the adult. Perturbation may occur by mutations in genes coding for essential components or as in the case of this invention, by selecting small compounds on the basis of their ability to specifically interfere the adult phenotype. Of equal importance is the fact that the myriad cellular signaling pathways are extremely active during this stage of Drosophila development due to imaginal disc development.

As previously discussed, the present invention discloses the utilization of a genetically-modified Drosophila strain which is specifically modified such that it possesses a gene (within a specific signaling pathway known to be involved in human diseases) which can be activated at a defined threshold level to produce an easily-detectable phenotype (e.g., the generation of an irregular, rough eye surface phenotype). This genetic modification may be produced by a naturally-occurring, non-wild-type allele of a specific gene which is isolated from a genetic mutagenesis screening assay well-known to those individuals skilled within the art. Alternatively, the genetic modification may be produced by genetic manipulation using genetic recombination/molecular biological techniques known to those skilled within the art. The preferred genetic modification is a non-wild-type allele which, when present in the heterozygous state, results in an altered phenotype that is dose dependent. As utilized herein, the term "dose dependent" is designated as meaning that the genetically-sensitized Drosophila strain exhibits an observably different phenotype for each specific genetic state when it possesses either none, one or two copies of the modified allele of the gene of interest.

The present invention utilizes the methodology of microinjection into the third instar larval developmental stage of genetically-modified Drosophila, thus permitting high-throughput screening (HTS) with subsequent automation of the assay procedure. This microinjection administration methodology offers several advantages over the conventional application by feeding. These advantages include, but not limited to: (i) both the time and developmental stage of the microinjection may be controlled in a precise manner; (ii) the amount, and thus the final concentration of the compound in vivo can be determined; (iii) the compound is rapidly dispersed through the open circulatory system and quickly reaches the target tissue, the imaginal discs; and (iv) the compounds are only administered at the time when the activity of the pathway is required to develop the easily scorable phenotype.

The HTS-based small molecular weight compound screening assay of the present invention is designed to ascertain (i.e., scores for) both the ability of the compound-treated larvae to undergo subsequent development (i.e., pupation) and for their eventual phenotype upon eclosion, in comparison to the mock-treated control Drosophila strain. The use of such in vivo assays allows for the highly relevant analysis of the bioavailability, biological/therapeutic function and toxicity of the compound(s) being tested. The present invention differs from conventional, HTS assays (based upon both cell-free or in vitro cell-based assay systems) in a number of ways including, but not limited to: (i) its overall degree of versatility; (ii) its indigenous screening capacity for compound specificity and non-toxicity and (iii) its lack of bias for specific classes of drug targets.

Without automation, the HTS-based small molecular weight compound screening assay of the present invention is capable of screening up to 100,000 compounds in a 1–2 month period. In contrast, with the use of an automated assay procedure, approximately 100,000 compounds may be screened in as little as 1–2 weeks. It should also be possible to scale up throughput with automated screening involving computer-assisted pattern recognition.

A wide variety of small molecular weight compounds may be used in the screen. Such compounds include, but are not limited to, any compositions which are being tested for lead drug discovery or development. Compounds may be aqueous- or lipid-soluble. Compounds may be delivered individually to separate Drosophila larvae or may be delivered to separate larvae as one of a plurality of different chemical compounds contained within a reagent solution, such as is performed within a multiplexing schema. Compounds may be dissolved or suspended within solution, or affixed to a solid-support. Solid supports may include, but are not limited to, insoluble polymer beads or a polymeric matrix coated with one or a plurality of individual compounds, or with combinatorial chemistries. Dosages and volumes which are microinjected into the Drosophila larvae may be varied so as to optimize dosages for further studies or to rank compounds as to their toxicity and/or potency. Information resulting from said variations in conditions may be used to prioritize chemicals for further study, to delineate the relative toxicities of structurally related chemicals, and/or to identify the proper dose range for subsequent toxicity studies (see e.g., Harris, et al., Fundam. Appl. Toxicol. 19:186–196).

In one embodiment of the present invention, recombinant DNA methodologies will be utilized to express exogenous genes which are functionally-linked to cell-specific transcriptional regulatory sequences. In an additional embodiment, exogenous genes which encode human homologs of the genes involved in the signaling pathway of interest will be utilized, so as to enable "humanization" of the aforementioned disease pathways. A preferred embodiment of the present invention involves the targeting of cell-specific expression of the incorporated exogenous genes to the cells of the Drosophila imaginal discs. Such genetic alterations possess the ability to greatly vary the genetic capabilities of the cells.

Compounds which are screened by use of the methodology disclosed in the present invention may be useful as analgesics and/or for the treatment of inflammatory disease, especially in the case of the azotricyclic compounds acting as antagonists of the neurokin 1/brandykin receptor. Members of the benzodiazopine library may be useful as a muscle relaxant and/or tranquilizer and/or as a sedative. Members of the 23 million Mixed Amide Library may be of use in the treatment of hypertension on endothelin antagonists or Raynaud's syndrome.

The carbon-carbon backbone of the compounds of the present invention may be saturated or unsaturated, cyclic or linear. These aforementioned compounds include, but are not limited to, carbohydrates, polyalcohols (e.g., ethylene glycol and glycerol) and polyphenols (e.g., hydroquinones and tetracylines). Carbohydrate- and polysaccharide-transformed compounds are defined herein so as to include all chemical moieties possessing a saccharide unit or which are transformed from a saccharide. These compounds may also include glycopeptides, glycolipids and other biopolymers (or biomacromolecules) containing saccharides, either in their entirety or as part of the molecular framework. The term carbohydrates merely represent a portion of a much larger family of polyhydroxylated organic compounds which are within the scope of the present invention. In addition, the carbohydrated/polyhydroxylated organic compounds of the present invention include, but are not limited to: monomeric acyclic compounds (e.g., ethylene glycol, glycerol and 1,2,3-trihydroxy pentane); polymeric acyclic compounds (e.g., di- or tri-ethylene diglycol; monomeric cyclic compounds (e.g., inositol and 1,2,3-trihydroxycyclopentane); polymeric cyclic compounds (e.g., di-inositol); polymeric and monomeric unsaturated compounds (e.g., tetrahydroxy-1,4-quinone) and polyphenols (e.g., tetracyclines) and derivatives, analogs and fragments thereof.

With respect to the generation of the small molecular weight compound libraries of the present invention, the combination of biochemical diversity is often synergistic with the metabolic diversity obtained from the in vivo production of "natural products". Collections of starting compounds, for example peptides, can be administered to cultures of microorganisms. In accord, each microbial strain may potentially create numerous modified peptides or peptide byproducts, thus generating a "metabolite library". Because each of these aforementioned cultures would (potentially) contain a very complex mixture of metabolites, a highly efficacious method of screening would be required (i.e., HTS). An aliquot of the library is incubated with each of the many strains typical of a microorganism fermentation screening program, and the media screened utilizing an HTS-based assay. In another aspect of the invention, natural product diversity is screened by creating a mixture of combinatorially-tagged liposomes; wherein each liposome preferable encapsulates only one member or a simple mixture of a natural product compound library. The libraries which are generated by the methodologies disclosed herein may be screened for any biological activity known within the art. These include, but are not limited to: anti-microbial activity, anti-tumor activity, enzyme inhibiting activity, receptor binding, growth promotion activity, and in vitro and in vivo tests for biological responses. Compounds may be based on naturally occurring extracellular or intracellular signaling molecules or their derivatives or the like (see, e.g., Alberts, et al., 1989. "Chapter 12: Cell Signaling." $2^{nd}$ Edition. Garland Publishing, Inc., New York, N.Y., pp. 681–726).

Unfortunately, many peptidic-based compounds possess unfavorable pharmacodynamic properties such as poor oral bioavailability and rapid clearance in vivo, which have tended to limit the more widespread development of these compounds as potential therapeutic agents. This realization, however, has recently inspired workers to extend the concepts of combinatorial organic synthesis beyond peptide chemistry to create libraries of known pharmacophores (e.g., benzodiazepines; see e.g., Bunin, et al., 1992. J. Amer. Chem. Soc. 114:10997–10998), as well as polymeric molecules such as oligomeric N-substituted glycines (i.e., peptoids) and oligocarbamates (see e.g., Dower, et al., U.S. Pat. No. 5,639,603).

The invention does not preclude the use of any type of compound library. Each library has its own specific advantages and disadvantages.

EXAMPLES

Example 1

Microinjection of Third Instar *Drosophila Melanogaster* Larvae

*Drosophila melanogaster* which had been previously genetically-modified to activate a disease-related morphogenetic pathway in the developing compound eye are mated. Eggs are collected on a nylon mesh by use of standard techniques known within the art and placed onto standard fly food. Approximately three to five day old larvae (third larval instar) are then collected and placed in the reservoir for the automated injection robot. Larvae are transported on a conveyer belt and immobilized through cooling to 10° C. Larvae are injected through the cuticle into the hemolyniph with defined amounts of each compound using a hypodermic needle of 20 μm internal diameter.

Following injection, the larvae are placed into glass vials for completion of their development. After eclosion, the adult flies are anesthetized with $CO_2$ and visually inspected utilizing a dissecting microscope. The parameters which are scored include: (i) the overall toxicity of the compound (determined by the number of survivors compared to mock injected larvae); and (ii) the modification of the genetically-modified Drosophila phenotype. For example, in the case of the raf phenotype, the genetic modification which is scored is the suppression or enhancement of the irregular rough eye morphology.

Example 2

Generation of Drosophila Raf Mutants

Su(Raf) and E(Raf) mutations were initially isolated by virtue of their ability to dominantly modify the rough eye phenotype in transgenic Drosophila carrying the activated Raf construct $Raf^{torY9}$ (see e.g., Dickson, et al., 1996. Genetics 142:163–171). FIG. 2 represents a schematic illustration of the known or estimated cytological chromosomal locations of all six Su(Raf) and two E(Raf) complementation groups (loci) (see e.g., Dickson, et al., 1996. Genetics 142:163–171). The $Raf^{torY9}$ fusion produced was identical to that previously described (see e.g., Dickson, et al. 1992. Nature 360:600–603) with the exception that it contained the weakly-activating Y9 mutation in the Torso extracellular domain (see e.g., Sprenger & Nusslein-Volhard, 1992. Cell 71:987–1001). Two different Raf$^{torY9}$ transgenic lines were used in this screening assay. The first was comprised of a second chromosomal insertion of a construct in which Raf$^{torY9}$ is expressed under the control of a single sev enhancer and the heat-inducible hsp70 promoter. This insertion is lethal in homozygotes. Drosophila carrying this chromosome balanced over the CyO balancer were used for the first rounds of mutagenesis and the Cy$^+$ progeny were scored. Subsequent rounds were performed using Drosophila homozygous for a chromosome 2 carrying a Raf$^{torY9}$ fusion construct expressed under a duplicated sev enhancer and the sev promoter (see e.g., Dickson, et al., 1996. Genetics 142:163–171). The two Raf$^{torY9}$ constructs were found to produced phenotypes of identical strength in heterozygotes. The first number of each allele indicated the round of mutagenesis in which the allele was isolated (i.e., numbers from 1–7 were isolated using the first construct and numbers 8–22 with the second construct). The phyl alleles 3G6 1 7L1 and 20Q1 have also been referred to as phyl$^1$, phyl$^2$ and phyl$^3$, respectively (see e.g., Dickson, et al., 1995. Cell 80:453–462).

The first rounds (rounds 1–7) of mutagenesis were performed by mutagenizing w$^{118}$ males isogenized for chromosome 2; whereas subsequent rounds (rounds 8–22) were performed with males reisogenized for the major autosomes. Males were treated with EMS (see e.g., Lewis & Bacher, 1968. Drosophila Info. Service 43:193–194) and crossed to Raf$^{torY9}$ transfonmants. The efficiency of mutagenesis, as estimated by the induction of sex-linked lethal mutations, was consistently demonstrated to be on the order of ~0.60 lethal hits per major chromosomal arm.

Example 3

Isolation and Analysis of Modifiers of the Raf$^{torY9}$ Phenotyne by Genetic Means The following example shows the method by which genes that modify a given pathway of choice can be identified using genetic means. In the manner of the invention described supra, corresponding small molecular weight compounds that modify a given pathway of choice will be used with the resulting genetically modified Drosophila strains to identify biologically active "lead" compounds.

The Raf kinase may be activated either by truncation of its amino-terminal domain (see e.g., Stanton, al., 1989. Mol. Cell Biol. 9:639–647) or by relocation of the entire protein to the cell membrane following post-translational modification at an artificial carboxyl-terminal CAAX site (see e.g., Leevers, et al., 1994. Nature 369:411–414; Stokoe, et al., 1994. Science 264:1463–1467). Similarly, the Drosophila Raf kinase is activated following anino-terminal truncation and relocation to the cell membrane via fusion to the extracellular and transmembrane domains of the Torso protein, a receptor tyrosine kinase (RTK) (see e.g., Dickson, et al. 1992. Nature 360:600–603). It should be noted that the Raf kinase activity of this aforementioned fusion protein may be further increased by introducing point mutations in the Torso extracellular domain which are analogous to dominantly activating mutations in the Torso RTK, tor$^{Y9}$ and tor$^{4021}$ (see e.g., Sprenger & Nusslein-Volhard, 1992. Cell 71:987–1001).

Transgenic Drosophila possessing the activated Raf construct Raf$^{torY9}$ expressed under the transcriptional control of an enhancer element of the sevenless (sev) gene were generated (see e.g., Basler, et al., 1991. Cell 64:1069–1081). In these transgenic Drosophila, the Raf kinase was found to be constitutively activated in the five cells of the developing eye which choose between the alternative fates of development as an R7 photoreceptor or a non-neuronal cone cell. Typically, Raf is activated in only one of these five cells (i.e., the R7 precursor) via the local activation of the sev RTK. Hence, activation of Raf is both necessary and sufficient for this cell type to select the R7 fate (see e.g., Dickson, et al., 1992. Genetics 142:163–171). In Raf$^{torY9}$ Drosophila mutants, ectopic Raf activity within the cone cell precursors results in some of these cells also developing as R7 cells. As a result, most of the 800 ommatidia found within the Drosophila compound eye were found to contain several, instead of just one, R7 photoreceptors. This result is illustrated in FIG. 1 (panel F) and these abnormal ommatidia disrupt the regular hexagonal ommatidial lattice. The Drosophila eye thus acquires a "roughened" external appearance, readily observed in live, anaesthetized flies (see FIG. 1, panel B). The degree of roughening generally reflects the average number of additional R7 cells per ommatidium, and thus provides an indirect measure of the efficiency of Raf signaling within the cone cell precursors. This observation would thus allow for the identification of "lead" compounds which dominantly-modify the degree of roughening and thus potentially affect some step within the cellular signaling pathway between Raf activation and the selection of the R7 fate.

Example 4

Interactions with a Hypomorphic Raf Allele

The following example shows the method by which genes that modify a given pathway of choice can be identified using genetic means. In the manner of the invention described supra, corresponding small molecular weight compounds that modify a given pathway of choice will be used with the resulting genetically modified Drosophila strains to identify biologically active "lead" compounds.

A complementary screen was performed in which mutations that dominantly-modify the phenotype of a gain-of-function (GOF) raf allele affecting only R7 cell development were isolated. The primary advantage of this approach is that, by specifically-addressing R7 development, it was possible to avoid complications with the formation of lethal genetic Drosophila mutations. Additionally, this type of approach also permitted simultaneously screening for both suppressor Su(Raf) and enhancer E(Raf) mutations. Thus, both positive and negative regulators may potentially be identified with a far greater degree of efficiency by the recovery of LOF alleles.

The gain-of-function (GOF) construct Raf$^{torY9}$, provided a convenient means for isolating interacting mutations. There is some evidence, however, that these aforementioned mutations may interact specifically with this construct (e.g., with either the sev enhancer or Torso domain) and not with the Raf kinase itself. It was therefore necessary to test each Su(Raf) and E(Raf) locus for genetic interactions with the hypomorphic raf allele, raf$^{HM7}$. The raf$^{HM7}$ allele produces reduced levels of the wild-type protein, sufficient for Drosophila survival at 18° C. but not at 25° C. (see e.g., Melnick, et al., 1993. Development 118:127–138). Raised at the permissive temperature of 18° C., only 50% of ommatidia in the eyes of hemizygous raf$^{HM7}$ Drosophila males were found to contain an R7 cell (see e.g., Dickson, et al., 1992. Nature 360:600–603).

Various result scenarios are possible. For example, if it was demonstrated that the Su(Raf) mutations impaired signaling via Raf, it would be expected that they would enhance the raf$^{HM7}$ phenotype. If it was found that the Su(Raf) mutations are generally required for Raf function, this may result in a synthetic lethality (i.e., non-allelic, non-complementation) at 18° C. On the other hand, if the Su(Raf) mutations were demonstrated to be specifically required for Raf function within the Drosophila eye, it would be expected that they would enhance the raf$^{HM7}$ eye phenotype without affecting the viability of these flies. Conversely, E(Raf) mutations, if they were demonstrated to relieve negative influences on Raf signaling, it would be expected that they would suppress the raf$^{HM7}$ phenotype.

As illustrated in Table 1, four of the Su(Raf) loci were found to enhance the raf$^{HM7}$ phenotype in accordance with these aforementioned predictions. Of these loci, three (rl, Su(Raf)3A and Su(Raf)3B) are synthetically lethal in combination with raf$^{HM7}$, thus suggesting that they encode proteins generally required for signal transduction via Raf In agreement with this prediction, rl has also been shown to encode a MAPK homologue required in several signaling events involving Raf (see e.g., Biggs, et al., 1994. EMBO J. 13:1628–1635; Brunner, et al., 1994. Nature 370:386–389). The fourth of these loci,phyl, enhances only the eye phenotype of raf$^{HM7}$, which was demonstrated to significantly increases the number of ommatidia lacking R7 cells (see e.g., Dickson, et al., 1995. Genes Dev. 6:2327–2339). This finding is consistent with the interpretation disclosed herein of phyl as a target gene transcriptionally-regulated only within R7 cells and two other photoreceptors, in response to activation of the Raf pathway. It should be noted that, at present, there is no evidence for phyl acting as a target gene for Raf signaling in any other tissue. The other two Su(Raf) loci—Su(Raf)2A and Su(Raf)3C—show no dominant genetic interaction with raf$^{HM7}$.

Somewhat surprisingly, neither of the E(Raf) loci were found to suppresses raf$^{HM7}$, but rather enhance the hypomorphic raf phenotype, resulting in synthetic lethality. The E(Raf)2A allele 1401 appears to be weaker than the other two alleles at this locus, and a small number of flies of the genotype raf$^{HM7}$/Y ; 1401/+eclose. Additionally, the raf$^{HM7}$ eye phenotype is also slightly enhanced in these flies. Since the E(Raf) mutations enhance the phenotypes of both LOF and GOF raf alleles, it is considered to be unlikely that these genetic interactions reflect direct biochemical interactions between the proteins these genes encode and Raf Example 5

Homozygous Su(Raf) and E(Raf) Phenotypes

The following example shows the method by which genes that modify a given pathway of choice can be identified using genetic means. In the manner of the invention described supra, corresponding small molecular weight compounds that modify a given pathway of choice will be used with the resulting genetically modified Drosophila strains to identify biologically active "lead" compounds.

The recessive phenotypes of rl, phyl and Star mutations have been reported elsewhere (see e.g., Heberlein, et al., 1993. Dev. Biol. 144:353–361; Biggs, et al., 1994. EMBO J. 13:1628–1635; Chang, et al., 1995. Cell 80:463–472; Dickson, et al., 1995. Genes Dev. 6:2327–2339). The rl phenotype appears to be required for the development of all eight photoreceptors; whereas phyl is required specifically for R1, R6 and R7. However, there is only circumstantial evidence for a role of Star in R7 development (see e.g., Kolodkin, et al., 1994. Development 120:1731–1745), but in any case the recovery of a Star allele in our screen is more likely due to its dominant rough eye phenotype than a specific interaction with Raf$^{torY9}$.

Surprisingly, three of the Su(Raf) genes do not appear to be absolutely required for development either of R7 or any other photoreceptor. The single Su(Raf)3B and Su(Raf)3C alleles are both viable in the homozygous condition and show no obvious defects in eye development. Su(Raf)2A mutations are homozygous lethal, but patches of homozygous mutant tissue could readily be recovered in heterozygous animals using the FLP/FRT technique to induce site-specific mitotic recombination (see Xu & Rubin, 1993. Development 117:1223–1237). Examination of such homozygous Su(Raf)2A clones shows that, although required for viability, this gene is dispensable for normal Drosophila eye development.

Su(Raf)3A mutations were also demonstrated to be lethal in the homozygous state, and it proved to be impossible to generate Su(Raf)3A mutant clones by mitotic recombination by use of the methodologies of the present invention.

This suggests that Su(Raf)3A, like raf and rl, may also be required for cell proliferation (see e.g., Nishida, et al., 1988. EMBO J. 7:775–781; Biggs, et al., 1994. EMBO J. 13:1628–1635). The requirement of Su(Raf)3A in the early proliferative phase of eye development precludes a direct examination of its role in the later stages of eye development during which cell fates are determined.

In conclusion, E(Raf)2A has been demonstrated to be required for both viability and eye development Homozygous mutant ommatidia were found to be of variable composition, often lacking either R7 or one or more other photoreceptors, but also occasionally containing extra photoreceptors of either class.

Example 6

Su(Raf)2A is Required for Ectopic R7 Development

The following example shows the method by which genes that modify a given pathway of choice can be identified using genetic means. In the manner of the invention described supra, corresponding small molecular weight compounds that modify a given pathway of choice will be used with the resulting genetically modified Drosophila strains to identify biologically active "lead" compounds.

Interestingly, it was found that the elimination of one copy of Su(Raf)2A severely impairs signaling via Raf$^{torY9}$; whereas elimination of both copies of the gene did not appear to affect signaling via the endogenous Raf kinase. One possible explanation of this result would be that Su(Raf)2A encodes a protein that interacts specifically with the activated Raf$^{torY9}$ fusion protein but not at all with the endogenous Raf. To test this hypothesis, Su(Raf)2A clones were generated in genetic backgrounds in which the Raf pathway is constitutively activated at points further upstream, i.e., at Sev in Sev$^{S11}$ transformants; (see e.g., Basler, et al., 1991. Cell 64:1069–1082) and at Ras1 in Ras1 V12 transformants (see e.g., Fortini, et al., 1992. Nature 355:559–561). This aforementioned assay resulted in the formation of ectopic, but not endogenous R7 cells is completely blocked within the Su(Raf)2A clone. This observation argues strongly against a specific interaction between Su(Raf)2A and Raf$^{torY9}$ and suggests that the protein encoded by Su(Raf)2A is indeed important for signaling via the wild-type Raf kinase, at least for the generation of ectopic R7 cells due to constitutive activation of the pathway at or above Raf.

Ectopic R7 cells are also formed in yan mutants in an independent manner from the Raf pathway (see e.g., Lai, et al., 1992. Cell 70:609–620). It is believed that the Raf/MAPK pathway acts in part to overcome the inhibitory influence on R7 development normally exerted via the Yan protein (see e.g., Brunner, et al., 1994. Nature 370:386–389; O'Neill, et al., 1994. Cell 78:137–147; Rebay, et al., Cell 81:857–866). The formation of extra R7 cells in yan mutants is also independent of Su(Raf)2A, thus suggesting that in Su(Raf)2A mutant tissue the pathway leading to ectopic R7 development is blocked at some point between Raf and Yan.

Specific embodiments have been exemplified herein for purposes of illustration only, and are not intended to be limiting with respect to the scope of the appended claims. In particular, various substitutions, alterations, and/or modifications may be made to the invention without departing from the spirit and scope of the invention as defined by the claims.

What is claimed is:

1. A method of screening for a non-mutagenic compound, said method comprising:
    (a) providing at least one larva from a Drosophila so, wherein said Drosophila strain is characterized by a genetic modification affecting at least one detectable phenotype of at least one adult structure derived from an i f disk, wherein said phenotype is modified by the number of functional copies of at least one gene present in said larva, such that altered levels of the protein expressed by the functional copy of the gene in the larva affects said phenotype;
    (b) microinjecting at least one candidate non-mutagenic compound, alone or in combination, into the open circulatory system (hemolymph) of at least one genetically modified Drosophila larva;
    (c) allowing said microinjected Drosophila larva to undergo pupation to develop into an adult organism comprising the adult structure formed from the imaginal disk and
    (d) analyzing the phenotype of at least one adult structure of the treated Drosophila larva and compare said phenotype to that in at least one untreated larva; wherein a difference in the visible phenolpic effect between the treated and untreated Drosophila indicates that the non-mutagenic compound modulates activity of at least one protein involved in establishing the adult sure.

2. The method of claim 1, wherein the insect's adult structure formed from the imaginal disk is the compound eye.

3. The method of claim 1, wherein said phenotypic effect is the effect of said microinjected compound on the irregular rough eye phenotype of the genetically-modified Drosophila strain.

4. The method of claim 1, wherein said compounds are synthetic chemical compounds.

5. The method of claim 1, wherein said compounds, which may be natural products, non-natural products or combinations thereof, are selected from the group consisting of: amino acids, polypeptides, proteins, nucleotides, carbohydrates, lipids, steroids, coenzymes, enzyme inhibitors, ligands and pharmaceuticals such as anti-hypertensive agents, anti-ulcer drugs/H2-receptor antagonists, anti-fungal agents, cholesterol-demethylase inhibitors, anxiolytic agents, analgesics, antibiotics, anti-inflammatory agents, contraceptives, abortifacients, anti-histamines, anti-tussive agents and sedatives, as well as modifications, derivatives and analogs thereof.

6. The method of claim 1, wherein said compounds are affixed onto an insoluble, solid support matrix by linkages which are cleavable by alteration of the physical environment of said matrix.

7. The method of claim 1, wherein said genetic modification of Drosophila is comprised of modification of a chromosomal sequence which is related to, and functions in, a disease system or pathway.

8. The method of claim 7, wherein said disease system or pathway is a human disease system or pathway.

9. The method of claim 1, wherein said genetic modification of Drosophila is comprised of modification of one or more gene(s) selected from the group consisting of: a Raf proto-oncogene pathway; a Ras proto-oncogene pathway; a WNT tumor suppressor pathway; a retinoblastoma tumor suppressor (Rb) pathway; c-src proto-oncogene pathway; c-Jun proto-oncogene pathway; c-myc proto-oncogene pathway; p53; and a c-abl proto-oncogene pathway.

10. The method of claim 1, wherein said microinjection procedure is automated.

11. The method of claim 1, wherein said screening method comprises a high-throughput screening procedure that is automated.

12. The method of claim 1, wherein the genetically-modified Drosophila larva is a third instar larva.

13. The method of claim 17, wherein said genetic modification of Drosophila is comprised of modification of one or more gene(s) selected from the group comprising: a Raf gene; a Ras proto-oncogene system or pathway; a WNT tumor suppressor system or pathway;, a hedgehog development regulator (HH) system or pathway; a sonic hedgehog development regulator (SHH) system or pathway; a retinoblastoma tumor suppressor (Rb) system or pathway; an activated Drosophila protein kinase B (PKB/AKT) gene; an activated human PKB/AKT gene; an activated insulin receptor gene; an insulin receptor substrates (IRS) gene or pathway; c-src proto-oncogene or pathway; c-Jun proto-oncogene or pathway; c-myc proto-oncogene or pathway, p53; Janus kinases (JAK/STAT pathway); nitric oxide (NO); calmodulin; cAMP dependent protein We (PKA) or pathway; $Ca^{2+}$ dependent protein kinase (PKC) or pathway, growth factors such as GH, TGF, PDGF and the like; receptor tyrosine kinases (RTKs) and pathways; interferons (IFN) or pathways; lipid metabolites or pathway; steroid hormones or pathway, phosphatidylinositol or pathway; G-protein coupled receptors or pathways; c-abl proto-oncogene or pathway; TGF-β and Smad gene family members; interleukins or pathway; GTPases or pathway; and ionophores or pathway.

14. A method of screening for a non-mutagenic compound, said method comprising:
    (a) providing at least one larva from a Drosophila strain, wherein said Drosophila strain is characterized by a genetic modification affecting at least one undetectable phenotype of at least one adult structure derived from an imaginal disk wherein said phenotype is modified by the number of functional copies of at least one gene present i said larva, such that altered levels of the protein expressed by the functional copy of the gene in the larva affects said phenotype;
    (b) microinjecting at least one candidate non-mutagenic compound, alone or in combination, into the open circulatory system (hemolymph) of at least one genetically modified Drosophila larva;
    (c) allowing said microinjected Drosophila larva to undergo pupation to develop into an adult organism comprising the adult structure formed from the imaginal disk; and (d) analyzing the phenotype of at least one adult structure of the treated Drosophila larva and comparing said phenotype to that in at least one untreated larva;

wherein a difference in the visible phenotypic effect between the treated and untreated Drosophila indicates that the non-mutagenic compound modulates activity of at least one protein involved in establishing the adult structure.

15. The method of claim 14, wherein the insect's adult structure formed from the imaginal disk is the compound eye.

16. The method of claim 14, wherein said phenotypic effect is the effect of said microinjected compound on the irregular rough eye phenotype of the genetically-modified Drosophila strain.

17. The method of claim 14, wherein said compounds are synthetic chemical compounds.

18. The method of claim 14, wherein said compounds, which may be natural products, non-natural products or combinations thereof, are selected from the group consisting of: amino acids, polypeptides, proteins, nucleotides, carbohydrates, lipids, steroids, coenzymes, enzyme inhibitors, ligands and pharmaceuticals such as anti-hypertensive agents, anti-ulcer drugs/H2-receptor antagonists, anti-fungal agents, cholesterol-demethylase inhibitors, anxiolytic agents, analgesics, antibiotics, anti-inflammatory agents, contraceptives, abortifacients, anti-histamines, anti-tussive agents and sedatives, as well as modifications, derivatives and analogs thereof.

19. The method of claim 14, wherein said compounds are affixed onto an insoluble, solid support matrix by linkages which are cleavable by alteration of t he physical environment of said matrix.

20. The method of claim 14, wherein said genetic modification of Drosophila is comprised of modification of a chromosomal sequence which is related to, and functions in, a disease system or pathway.

21. The method of claim 7, wherein said disease system or pathway is a human disease system or pathway.

22. The method of claim 14, wherein said genetic modification of Drosophila is comprised of modification of one or more gene(s) selected from the group consisting of: a Raf proto-oncogene pathway; a Ras proto-oncogene pathway; a WNT tumor suppressor pathway, a retinoblastoma tumor suppressor (Rb) pathway; c-src proto-oncogene pathway; c-Jun proto-oncogene pathway; c-myc proto-oncogene pathway, p53, and a c-abl proto-oncogene pathway.

23. The method of claim 14, wherein said microinjection procedure is automated.

24. The method of claim 14, wherein said screening procedure is a high-throughput screening procedure that is automated.

25. The method of claim 14, wherein the genetically-modified Drosophila larva is a third instar larva.

26. The method of claim 14, wherein said genetic modification of Drosophila is comprised of modification of one or more gene(s) selected from the group comprising: a Raf gene; a Ras proto-oncogene system or pathway; a WNT tumor suppressor system or pathway, a hedgehog development regulator (HH) system or pathway; a sonic hedgehog development regulator (SHH) system or pathway; a retinoblastoma tumor suppressor (Rb) system or pathway; an activated Drosophila protein kinase B (PKB/AKT) gene; an activated human PKB/AKT gene; an activated insulin receptor gene; an insulin receptor substrates (IRS) gene or pathway, c-src proto-oncogene or pathway; c-Jun proto-oncogene or pathway; c-myc proto-oncogene or pathway; p53; Janus kinases (JAK/STAT pathway); nitric oxide (NO); calmodulin; cAMP dependent protein kinase (PKA) or pathway, $Ca^{2+}$ dependent protein e (PKC) or pathway; growth factors such as GH, TGF, PDGF and the like; receptor tyrosine kinases (RTKs) and pathways; interferons (IFN) or pathways; lipid metabolites or pathway; steroid hormones or pathway; phosphatidylinositol or pathway, G-protein coupled receptors or pathways; c-abl proto-oncogene or pathway; TGF-β and Smad gene family members; interleukins or pathway; GTPases or pathway, and ionophores or pathway.

* * * * *